United States Patent
Spatola et al.

(10) Patent No.: US 6,551,998 B1
(45) Date of Patent: Apr. 22, 2003

(54) ANTIMICROBIAL AGENTS

(75) Inventors: Arno F. Spatola, Louisville, KY (US); James Jun Wen, Dayton, NJ (US); David M. Vogel, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

(21) Appl. No.: 09/599,787

(22) Filed: Jun. 22, 2000

Related U.S. Application Data

(60) Provisional application No. 60/140,208, filed on Jun. 22, 1999.

(51) Int. Cl.⁷ .................. A61K 38/07; A61K 38/08; C07K 5/04; C07K 7/02; C07K 7/06
(52) U.S. Cl. ............. 514/17; 514/15; 514/16; 514/18; 530/323; 530/327; 530/328; 530/329; 530/330; 530/331
(58) Field of Search .............. 514/15, 16, 17, 514/18; 530/323, 327, 328, 329, 330, 331, 332

(56) References Cited

U.S. PATENT DOCUMENTS

| | | | |
|---|---|---|---|
| 4,543,252 A | 9/1985 | Lehrer et al. | 514/12 |
| 4,559,157 A | 12/1985 | Smith et al. | 252/90 |
| 4,608,392 A | 8/1986 | Jacquet et al. | 514/844 |
| 4,659,692 A | 4/1987 | Lehrer et al. | 514/12 |
| 4,705,777 A | 11/1987 | Lehrer et al. | 514/12 |
| 4,820,508 A | 4/1989 | Wortzman | 424/59 |
| 4,938,949 A | 7/1990 | Borch et al. | 424/10 |
| 4,992,478 A | 2/1991 | Geria | 514/782 |
| 5,854,211 A * | 12/1998 | Johansen et al. | 514/8 |

FOREIGN PATENT DOCUMENTS

| | | | |
|---|---|---|---|
| EP | 0162161 | 11/1985 | C07K/7/10 |
| EP | 0193351 | 9/1986 | C07K/7/10 |
| EP | 443559 A2 * | 8/1991 | |
| WO | 89/11291 | 11/1989 | A61K/37/02 |
| WO | 96/34005 | 10/1996 | C07H/15/24 |
| WO | 97/03995 | 2/1997 | C07H/15/24 |

OTHER PUBLICATIONS

De Lucca, A.J., et al., "Antifungal Peptides: Novel Therapeutic Compounds against Emerging Pathogens", *Antimicrobial Agents and Chemotherapy*, 43 (*1*), pp. 1–11, (Jan. 1999).

(List continued on next page.)

*Primary Examiner*—Jeffrey E. Russel
(74) *Attorney, Agent, or Firm*—Schwegman, Lundberg, Woessner & Kluth, P.A.

(57) ABSTRACT

Antimicrobial compounds of formula I are disclosed:

$$R_1—X—R_2$$

wherein

X is a group comprising of from about 4 to about 10 amino acids, wherein at least one of the amide (—CONH—) linkages is replaced by —$CR_aR_aR_bNR_c$—;

$R_a$, $R_b$, and $R_c$ are each independently hydrogen, ($C_1$–$C_6$) alkyl, ($C_2$–$C_6$)alkenyl, ($C_2$–$C_6$)alkynyl, ($C_3$–$C_8$) cycloalkyl, ($C_1$–$C_6$)alkoxycarbonyl, aryl, or heterocycle; and $R_1$ and $R_2$ are each independently hydrogen, a saccharide, a lipid, a solubilizing agent, or a suitable protecting group;

or a pharmaceutically acceptable salt thereof, as well as pharmaceutical compositions comprising such compounds or salts, and methods of using such compounds or salts to treat a bacterial infection.

12 Claims, 1 Drawing Sheet

BocE— Resin ⟶ BocDψ[$CR_aR_bNR_c$]E— Resin ⟶

⟶ BocCDψ[$CR_aR_bNR_c$]E— Resin ⟶

BocBCDψ[$CR_aR_bNR_c$]E— Resin ⟶ BocAψ[$CR_aR_bNR_c$]BCDψ[$CR_aR_bNR_c$]E— Resin ⟶ —Aψ[$CR_aR_bNR_c$]BCDψ[$CR_aR_bNR_c$]E—

OTHER PUBLICATIONS

Oh, J.E., et al., "Design, systhesis and characterization of antimicrobial pseudopeptides corresponding to membrane–active peptide", *Journal of Peptide Research, 54 (2)*, pp. 129–36, (Aug. 1999).

Spatola, A.F., "Peptide backbone modifications: a structure–activity analysis of peptides containing amide bond surrogates", *Chemistry & Biochemistry of Amio Acids, Peptides & Proteins, vol. 7, Chapter 5*, B. Weinstein, Ed., Marcel Dekker, NY, pp. 267–357, (1983).

Stemmer, C., et al., "Protection against lymphocytic choriomeningitis virus infection induced by a reduced peptide bond analogue of the H–2D$^b$–restricted CD8$^+$T cell epitope GP33", *Journal of Biological Chemistry, 274 (9)*, pp. 5550–5556, (Feb. 26, 1999).

Wen, J.J., et al., "A systematic approach to the solid–phase synthesis of linear and cyclic pseudopeptide libraries containing ψ[CH$_2$NH] amide bond surrogates", *Journal of Peptide Research, 49 (1)*, pp. 3–14, (1997).

* cited by examiner

SEQUENCE LISTING

<160> NUMBER OF SEQ ID NOS: 2

<210> SEQ ID NO 1
<211> LENGTH: 5
<212> TYPE: PRT
<213> ORGANISM: Artificial Sequence
<220> FEATURE:

```
<223> OTHER INFORMATION: An artificial peptide (see Table 1).
<221> NAME/KEY: SITE
<222> LOCATION: 1
<223> OTHER INFORMATION: Xaa = H-2-(1- or 2- naphthylalanine).

<400> SEQUENCE: 1

Xaa Lys Ser Phe Leu
 1               5

<210> SEQ ID NO 2
<211> LENGTH: 5
<212> TYPE: PRT
<213> ORGANISM: Artificial Sequence
<220> FEATURE:
<223> OTHER INFORMATION: An artificial peptide (see Table 1).
<221> NAME/KEY: SITE
<222> LOCATION: 1
<223> OTHER INFORMATION: Xaa = H-2-(1- or 2- naphthylalanine)psi[CH2NH]

<400> SEQUENCE: 2

Xaa Lys Ser Phe Leu
 1               5
```

ANTIMICROBIAL AGENTS

CROSS-REFERENCE TO RELATED APPLICATIONS

This application priority from U.S. Provisional Application No. 60/140,208, filed Jun. 22, 1999; the disclosure of which is incorporated by reference in its entirety.

GOVERNMENT FUNDING

The invention described herein was made with government support under Grant Number GM-33376 awarded by the National Institute of Health. The United States Government has certain rights in the invention.

BACKGROUND OF THE INVENTION

The worldwide use of antibiotics to treat infectious diseases in humans and animals has grown dramatically over the last forty years. In 1954, two million pounds of antibiotics were produced in the United States. Today, the figure exceeds 50 million pounds. According to the Centers Disease Control (CDC), humans consume 235 million doses of antibiotics annually. Widespread misuse or overuse of antibiotics has fostered the spread of antibiotic resistance and has contributed to the development of a serious public health problem. Antibiotic resistance occurs when bacteria that cause infection are not killed by the antibiotics taken to stop the infection. The bacteria survive and continue to multiply, causing more harm. For example, the bacterium *Staphylococcus aureus* is a major cause of hospital acquired infections that, historically, responded satisfactorily to the antibiotic vancomycin. Recently, however, many strains of *S. aureus* have been found to be resistant to vancomycin. Moreover, the death rate for some communicable diseases such as tuberculosis have started to rise again, in part because of increases in bacterial resistance to antibiotics.

The occurrence of antibiotic resistance in bacteria has spurred the search for new antibacterial compounds. In large part, this search for new drugs has focused on identifying the defense molecules that plants and animals themselves produce to fight infections. One group of compounds that has gained researchers' attention are the peptide antibiotics.

Both plants and animals fight infection by producing peptides that have antimicrobial and antiviral activity. They are typically characterized by their small size (less than 35 amino acid residues) and positive charge. It is hypothesized that these molecules disrupt cellular membranes of the bacteria. To that end, various classes of these antimicrobial/antiviral peptides have been isolated from tissues of plants bacteria, fungi, and animals. See A. J Deluca et. al. Antimicrob. Agents & Chemother., 43, 1–11 (review). Plant-derived antimicrobial peptides include the plant defensins. Bacterial and fungal-derived antimicrobial peptides include, among others, the iturins, syringomicins, nikkomicins, polyoxins.

Mammalian-derived antimicrobial peptides include the defensins, protegrins, and gallinacins. Defensins are small cationic proteins that are isolated from various organisms. They electrostatically bond to membranes, causing the formation of multimeric pores and the leakage of essential minerals and metabolites. Related to the defensins are the protegrins and gallinacins. Protegrins are cationic, cysteine-rich molecules that are isolated from porcine leucocytes. They form weakly selective ionic channels that allow membrane permeation of anions and small cations. Gallinacins are cationic, arginine and lysine-rich molecules that are isolated from chicken leucocytes. At least several patents have issued on the defensins, including U.S. Pat. Nos. 4,705,777; 4,659,692; and 4,543,252; EP 193351; EP 185250; EP 162161; and WO 8911291.

Insect-derived antimicrobial peptides include the cecropins. Cecropins are cationic linear peptides that are isolated from the hemolymph of the giant silk moth, *Hyalopora ceropia*. They have been observed to form time-variant voltage dependant ion channels in planar lipid membranes. Cecropins are not lethal to mammals and have been administered safely to animals. Cecropins are active fungicides against pathogenic Aspergillus species at between 25–100 µg/mL. Cecropin A exhibited total killing of *Fusarium moniliforme* and *Fusarium oxysporum* at 12.4 µg/mL. Several of the cecropins have been isolated and described in the patent literature. See, e.g., WO 8900199; WO 8805826; WO 8604356; and WO 8805826.

Amphibian-derived antimicrobial peptides include dermaseptin and the magainins. Dermaseptins are linear, cationic, lysine-rich peptides that are isolated from the South American arboreal frog, *Phyllomedusa sauvagii*. They are believed to lyse micro-organisms by interacting with lipid bilayers, leading to alterations in membrane function responsible for osmotic balance. Isolated from the African clawed frog *Xenopus laevis*, the magainins are helical ionophores that dissipate in cell membranes, causing lysis.

Although many of the antimicrobial peptides and peptide classes discussed in the previous paragraphs exhibit promising biological activity, their widespread adoption for use as pharmacological agents to fight infections in mammals has been somewhat slow. This is due in part to peptides possessing amide bonds that are hydrolyzable in the gut. In short, natural and synthetic peptides are not transported across the intestinal barrier.

As a result, there remains a need for peptide antibiotic derivatives that are less-hydrolyzable or non-hydrolyzable in the gut and that can be transported across the intestinal barrier. There is an additional need to identify compounds that possess the biological activity of antimicrobial peptides. There is also a need for pharmacological tools for the further study of the physiological processes associated with peptide-mediated disruption of cell membrane function and the use of antimicrobial peptides to fight infections in mammals.

SUMMARY OF THE INVENTION

This and other needs are met by the present invention. The present invention is directed to compounds that exhibit reduced levels of hydrolysis in the gut but that exhibit the biological activity of peptide antibiotics, particularly the antimicrobial peptides.

Accordingly there is provided a compound of the invention which is a compound of formula (I):

$$R_1-X-R_2 \qquad (I)$$

wherein

X is a peptide comprising of from about 4 to about 10 amino acids, wherein at least one of the amide (—CONH—) linkages is replaced by —CR$_a$C$_b$NR$_c$—;

R$_a$, R$_b$, and R$_c$ are each independently hydrogen, (C$_1$–C$_6$) alkyl, (C$_2$–C$_6$)alkenyl, (C$_2$–C$_6$)alkynyl, (C$_3$–C$_8$) cycloalkyl, (C$_1$–C$_6$)alkoxycarbonyl, aryl, heterocycle; and R$_1$ and R$_2$ are each independently hydrogen, a saccharide, a lipid, a solubilizing agent, or a protecting group;

or a pharmaceutically acceptable salt thereof.

The invention also provides a pharmaceutical composition comprising a compound of formula (I), or a pharmaceutically acceptable salt thereof, in combination with a pharmaceutically acceptable diluent or carrier.

Additionally, the invention provides a therapeutic method for preventing or treating antimicrobial infections in a mammal (e.g., a human) in need of such treatment comprising administering to the mammal an effective amount of a compound of the invention.

The invention also provides a compound of formula (I) for use in medical therapy (preferably for use in treating and/or preventing antimicrobial infections in a mammal), as well as the use of a compound of formula I for the manufacture of a medicament for the treatment of a pathological condition or symptom in a mammal, such as a human, which is associated with an antimicrobial infection.

DETAILED DESCRIPTION OF THE INVENTION

Figure 1:
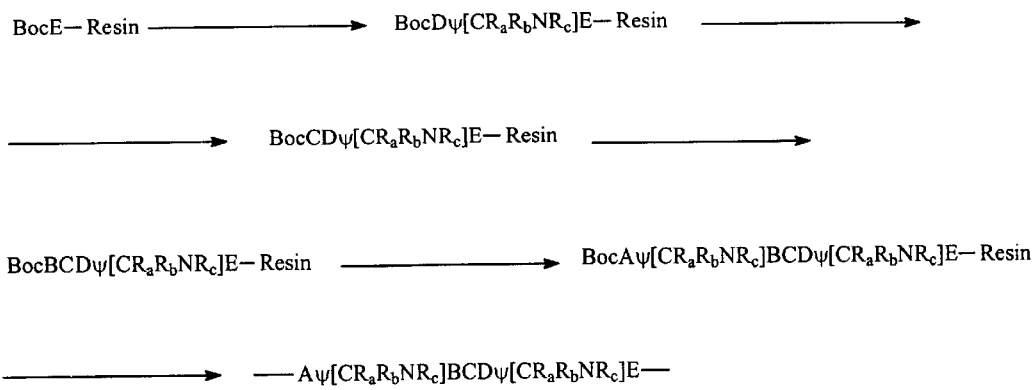
FIG. 1 illustrates the preparation of compounds of the invention.

The following definitions are used, unless otherwise described: halo is fluoro, chloro, bromo, or iodo. Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, $(C_1–C_4)$ alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

Specific and preferred values listed below for radicals, substituents, and ranges, are for illustration only; they do not exclude other defined values or other values within defined ranges for the radicals and substituents.

Specifically, $(C_1–C_6)$alkyl can be methyl, ethyl, propyl, isopropyl, butyl, iso-butyl, sec-butyl, pentyl, 3-pentyl, or hexyl; $(C_3–C_8)$cycloalkyl can be cyclopropyl, cyclobutyl, cyclopentyl, cyclohexyl, or $(C_3–C_6)$cycloalkyl. $(C_1–C_6)$ alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_2–C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl; $(C_2–C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

The term "antimicrobial" as used herein means that the compounds of the present invention inhibit, prevent, or destroy the growth or proliferation of microbes such as bacteria, fungi, viruses or the like. The term "antiviral" as used herein means that the compounds of the present invention inhibit, prevent or destroy the growth or proliferation of viruses or of viral-infected cells. The term "anti-tumor" as used herein means that the compounds of the present invention may be used to inhibit the growth of or destroy tumors. The term "antifungal" as used herein means that the compounds of the present invention may be used to inhibit the growth of or destroy fungi.

The term "peptide" includes linear peptides containing about four to about ten amino acids. The term "pseudopeptide" includes linear peptide wherein at least one of the amide (—CONH—) linkages connecting one amino acid to another has been replaced by an amine (—$CR_aR_bNR_c$—) linkage. The nomenclature of pseudopeptides wherein the amide linkage is replaced by an amine linkage are described by the use of the "psi-bracket" nomenclature (Spatola, 1983). The Greek letter psi (ψ) indicates that the normal amide moiety (CONH) between two adjacent amino acid alpha carbons has been replaced. The replacing unit is given within the brackets. Thus, the amine linkage of the pseudopeptides of the present invention is depicted as ψ[$CH_2NH$], as in Pheψ[$CH_2NH$]Leu. The complete structure of a typical compound such as compound 14 is given below:

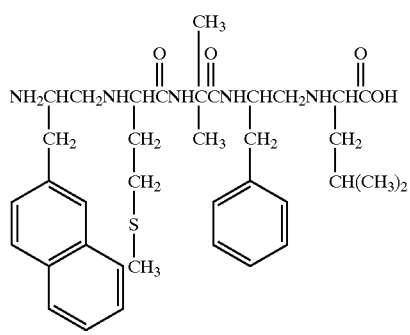

14

The term "amino acid" includes the residues of natural amino acids and also includes unnatural amino acids. The stereochemistry of the amino acids used for preparing the compounds of the present invention is specified with the D,L system, which is well-known to practitioners in the art.

Natural amino acid notations used herein are conventional and are as follows: Alanine (Ala), Arginine (Arg), Asparagine (Asn), Aspartic acid (Asp), Cysteine (Cys), Glutamine (Gin), Glutamic acid (Glu), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr), and Valine (Val). Unnatural amino acids used herein included 3- or 4-aminomethyl benzoic acid (3-Amb or 4-Amb), aminoisobutyric acid (Aib), 1- or 2-naphthylalanine (Nal), norleucine (Nle), and diethylglycine (Deg). The amino acid homoarginine, not encoded genetically, is abbreviated Har. Other unnatural amino acids include phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citrulline, α-methyl-alanine, para-benzoylphenylalanine, phenylglycine, propargylglycine, sarcosine, and tert-butylglycine.

The term "amino acid" also includes natural and unnatural amino acids bearing a conventional amino protecting group (e.g. acetyl or benzyloxycarbonyl), as well as natural and unnatural amino acids protected at the carboxy terminus (e.g. as a ($C_1$–$C_6$)alkyl, phenyl, phenethyl, or benzyl ester or amide; or as an a-methylbenzyl amide). Other suitable amino and carboxy protecting groups are known to those skilled in the art (See for example, T. W. Greene, T. W.; Wutz, P. G. M. *Protecting Groups In Organic Synthesis*, Second Edition, 1991, New York, John Wiley & sons, Inc, and references cited therein). Peptide sequences specifically recited herein are written with the amino terminus on the left and the carboxy terminus on the right. The term "saccharide" includes monosaccharides, disaccharides, trisaccharides and polysaccharides. Saccharide includes glucose, sucrose fructose and ribose, as well as deoxy sugars such as deoxyribose and the like. Saccharide also includes "C sugars," wherein the oxygen atom in the carbohydrate ring is replaced by a carbon atom. Saccharide derivatives can conveniently be prepared as described in International Patent Applications Publication Numbers WO 96/34005 and 97/03995. A saccharide can conveniently be linked to the remainder of a compound of formula I through an ether bond.

The term "lipid" includes hydrocarbons, which include ($C_1$–$C_{30}$) alkyl, ($C_2$–$C_{30}$) alkenyl, ($C_2$–$C_{30}$) alkynyl, ($C_3$–$C_{12}$) cycloalkyl, and aryl; substituted hydrocarbons, which include alcohols, aldehydes, fatty acids, soaps, acid-soaps, and amines; waxes and other simple esters of fatty acids; esters of fatty alcohols; esters of fatty acids, which include triacylglycerols, diacylglycerols, and monoacylglycerols; glycerophospholipids, which include phosphatidic acid, choline glycerophospholipids, serine glycerophospholipids, inositol glycerophospholipids, phosphatidylglycerols, and lysoglycerophospholipids; glycoglycerolipids; sphingolipids such as sphingosine, ceramide, sphingomyelin, sialoglycosphingolipids, and glycosylsphingolipids; steroids such as sterols, bile acids, cardiac glycosides, sex and adrenal hormones; and other lipids such as vitamins A, D, E, and K; eicosanoids, acyl CoA, acyl carnitine, glycosyl phosphatidyl inositols, lipopolysaccharides, and dolichols.

The term "solubilizing agent" includes agents that solubilize the compounds of the present invention under physiologic conditions. An example of a suitable solubilizing agent is polyethylene glycol and the like.

The term "treatment" as used herein includes any treatment of a condition or disease in an animal, particularly a mammal, more particularly a human and includes:

i. preventing the disease or condition from occurring in a subject which may be predisposed to the disease but is not yet diagnosed as having it;

ii. inhibiting the disease or condition; i.e., arresting its development; relieving the disease or condition; i.e., causing regression of the condition; or relieving the conditions caused by the disease; i.e., symptoms of the disease.

The amino terminus of any of the peptides of the present invention may be in the free amino form or may be acylated by a group of the formula RCO—, wherein R is ($C_1$–$C_6$) alkyl, ($C_2$–$C_6$) alkenyl, $C_2$–$C_6$(alkynyl), or ($C_3$–$C_8$) cycloalkyl. For example, R can be methyl, ethyl, 1-propyl, t-butyl, n-pentyl, cyclohexyl, cyclohexen-2-yl, cyclopentyl, hexen-3-yl, hexyn-4-yl, and the like. The amino terminus can also be alkylated with a group of formula R.

The C-terminus of the peptides of the invention may be in the form of the underivatized carboxyl group, either as the free acid or an acceptable salt, such as the potassium, sodium, calcium, magnesium, or other salt of an inorganic ion or of an organic ion such as caffeine. The carboxyl terminus may also be derivatized by formation of an ester with an alcohol of the formula ROH, or may be amidated by an amine of the formula $NH_3$, or $RNH_2$, or $R_2NH$, wherein each R is independently hydrocarbyl of 1–6 carbons as defined above. Peptides wherein the carboxy terminus is of the formula —COOH, or —$CONH_2$, or the salt are preferred. Amidated forms of the peptides wherein the C-terminus has the formula —$CONH_2$ are especially preferred.

Alternatively, the N- and C-terminus amino acids may be linked to saccharides, lipids, solubilizing agents, or protecting groups.

The compounds of the invention may also include compounds which are variations of those compounds specifically exemplified herein. The term "variation" as used herein denotes the replacement of an amino acid residue by another residue. Examples of variations include the substitution of an amino acid in the native L configuration for D amino acid. In the specific peptides shown in the present application, the L-configuration of any amino acid residue having an optical isomer is intended unless the D-configuration is expressly indicated by the letter D.

Another example of a variation is the replacement of one hydrophobic residue such as isoleucine, valine, leucine, alanine, cysteine, glycine, phenylalanine, proline, tryptophan, tyrosine, isoleucine or methionine for another, or the substitution of one polar residue for another, such as the substitution of arginine for lysine, glutamic for aspartic acids, or glutamine for asparagine, and the like. Neutral hydrophilic amino acids which can be substituted for one another include asparagine, glutamine, serine and threonine.

A further example of a variation is a sidechain variation such as the acylation of a nitrogen atom by procedures known in the art.

A further example of a variation is the replacement of an amino acid with a more rigid molecule, such as 3-aminomethylbenzoic acid or 4-aminomethylbenzoic acid.

In the peptides of the invention, one or more amide linkages (—CO—NH—) is replaced with an —$CR_aR_bNR_c$— linkage or a similar linkage that is capable of carrying a positive charge. This replacement can be made by methods known in the art. The following references describe preparation of peptide analogs which include these alternative-linking moieties: Spatola, A. F., Vega Data (March 1983), Vol. 1, Issue 3, "Peptide Backbone Modifications" (general review); Spatola, A. F., in "Chemistry and Biochemistry of Amino Acids Peptides and Proteins," B. Weinstein, eds., Marcel Dekker, New York, p. 267 (1983) (general review); Morley, J. S., Trends Pharm Sci (1980) pp. 463–468 (general review); Hudson, D., et. al., Int J Pept Prot Res (1979) 14:177–185 (—$CH_2NR$—).

Specific compounds of formula (I) of formula I are those compounds wherein X is:

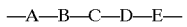

wherein each of A, B, C, D, E can be independently an amino acid.

A preferred group of compounds are compounds wherein each of A, B, C, D, and E is a natural amino acid. In addition, each of A, B, C, D, and E can be in the L configuration. Alternatively, one of A, B, C, D, or E can be in the D configuration.

Specific values for amino acid B in the compound A—B—C—D—E include lysine, methionine, diethylglycine, aminoisobutyric acid, and isoleucine.

Specific values for amino acid C in the compound A—B—C—D—E include serine, aminoisobutyric acid, phenylalanine, valine, diethylglycine, and aminomethylbenzoic acid.

A specific value for amino acid D in the compound A—B—C—D—E is phenylalanine.

A specific value for amino acid E in the compound A—B—C—D—E is leucine.

Especially preferred compounds are peptides wherein A in the compound A—B—C—D—E is naphthylalanine or aminomethybenzoic acid and E is leucine, B is lysine or methionine, and C is serine or aminomethyl benzoic acid.

An especially preferred group of peptides are peptides wherein the bond connecting A to B is replaced by —$CR_aC_bNR_c$—. Another especially preferred group of peptides are peptides wherein the bond connecting D to E is replaced by —$CR_aC_bNR_c$—. A most especially preferred group of peptides are peptides wherein the bonds connecting A to B and D to E are replaced by —$CR_aC_bNR_c$—. Specific peptides of the present invention are depicted in Table 1.

TABLE 1

Antimicrobial Compounds

| | |
|---|---|
| 1 | H-Nalψ[CH$_2$NH]Lys-Ser-Pheψ[CH$_2$NH]Leu-OH |
| 2 | H-Nalψ[CH$_2$NH]Lys-Val-Pheψ[CH$_2$NH]Leu-OH |
| 3 | H-Nalψ[CH$_2$NH]Lys-Phe-Pheψ[CH$_2$NH]Leu-OH |
| 4 | H-Nalψ[CH$_2$NH]Met-Ser-Pheψ[CH$_2$NH]Leu-OH |
| 5 | H-Nalψ[CH$_2$NH]Met-Val-Pheψ[CH$_2$NH]Leu-OH |
| 6 | H-Nalψ[CH$_2$NH]Met-Phe-Pheψ[CH$_2$NH]Leu-OH |
| 7 | H-Nalψ[CH$_2$NH]Ile-Ser-Pheψ[CH$_2$NH]Leu-OH |
| 8 | H-Nalψ[CH$_2$NH]Ile-Val-Pheψ[CH$_2$NH]Leu-OH |
| 9 | H-Nalψ[CH$_2$NH]Ile-Phe-Pheψ[CH$_2$NH]Leu-OH |
| 10 | H-Nalψ[CH$_2$NH]Aib-Ser-Pheψ[CH$_2$NH]Leu-OH |
| 11 | H-Nalψ[CH$_2$NH]Aib-Val-Pheψ[CH$_2$NH]Leu-OH |
| 12 | H-Nalψ[CH$_2$NH]Aib-Phe-Pheψ[CH$_2$NH]Leu-OH |
| 13 | H-Nalψ[CH$_2$NH]Lys-Aib-Pheψ[CH$_2$NH]Leu-OH |
| 14 | H-Nalψ[CH$_2$NH]Met-Aib-Pheψ[CH$_2$NH]Leu-OH |
| 15 | H-Nalψ[CH$_2$NH]Ile-Aib-Pheψ[CH$_2$NH]Leu-OH |
| 16 | H-Nalψ[CH$_2$NH]Deg-Ser-Pheψ[CH$_2$NH]Leu-OH |
| 17 | H-Nalψ[CH$_2$NH]Deg-Val-Pheψ[CH$_2$NH]Leu-OH |
| 18 | H-Nalψ[CH$_2$NH]Deg-Phe-Pheψ[CH$_2$NH]Leu-OH |
| 19 | H-Nalψ[CH$_2$NH]Lys-Deg-Pheψ[CH$_2$NH]Leu-OH |
| 20 | H-Nalψ[CH$_2$NH]Met-Deg-Pheψ[CH$_2$]Leu-OH |
| 21 | H-Nalψ[CH$_2$NH]Ile-Deg-Pheψ[CH$_2$]Leu-OH |
| 22 | H-D-2-Nalψ[CH$_2$NH]Lys-Ser-Pheψ[CH$_2$NH]Leu-OH |
| 23 | H-2-Nalψ[CH$_2$NAc]Lys-Ser-Pheψ[CH$_2$NH]Leu-OH |
| 24 | Ac-2-Nalψ[CH$_2$NH]Lys-Ser-Pheψ[CH$_2$NH]Leu-OH |
| 25 | H-2-Nalψ[CH$_2$NAc]Lys-Ser-Pheψ[CH$_2$NH]Leu-OH |
| 26 | H-2-Nal-Lys-Ser-Phe-Leu-OH |
| 27 | H-2-Nalψ[CH$_2$NH]Lys-Ser-Phe-Leu-OH |
| 28 | H-2-Nalψ[CH$_2$NH]Lys(Ac)-Ser-Pheψ[CH$_2$NH]Leu-OH |
| 29 | H-D-2-Nalψ[CH$_2$NH]D-Lys-D-Ser-D-Pheψ[CH$_2$NH]D-Leu-OH |
| 30 | H-2-Nalψ[CH$_2$NAc]Lys-Ser-Pheψ[CH$_2$NH]Leu-OH |
| 31 | H-2-Nalψ[CH$_2$NH]Met-Aib-Pheψ[CH$_2$NH]Leu-NH$_2$ |
| 32 | H-2-Nalψ[CH$_2$NH]Nle-Aib-Pheψ[CH$_2$NH]Leu-OH |
| 33 | H-2-Nalψ[CH$_2$NH]Met-4-AMB-Pheψ[CH$_2$NH]Leu-OH |
| 34 | H-2-Nalψ[CH$_2$NH]Met-3-AMB-Pheψ[CH$_2$NH]Leu-OH |
| 35 | H-D-2-Nalψ[CH$_2$NH]D-Met-Aib-D-Pheψ[CH$_2$NH]D-Leu-OH |
| 36 | H-2-Nalψ[CH$_2$NH]Lys-Ser-4-AMBψ[CH$_2$NH]Leu-OH |
| 37 | 4-AMBψ[CH$_2$NH]Lys-Ser-Pheψ[CH$_2$NH]Leu-OH |
| 38 | 4-AMBψ[CH$_2$NH]Lys-Ser-4-AMBψ[CH$_2$NH]Leu-OH |

Processes for preparing compounds of formula I are provided as further embodiments of the invention and are illustrated by the following procedures in which the meanings of the generic radicals are as given above unless otherwise qualified. Briefly, a compound of formula I can be synthesized by such commonly used methods as t-Boc or Fmoc protection of alpha-amino groups. Both methods involve stepwise syntheses whereby a single amino acid is added at each step starting from the C terminus of the peptide (See, Coligan, et al., Current Protocols in Immunology, Wiley Interscience, 1991, Unit 9).

Compounds of the invention can also be synthesized by the well known solid phase peptide synthesis methods and described Merrifield, J. Am. Chem. Soc., 85:2149, 1962), and Stewart and Young, Solid Phase Peptides Synthesis, (Freeman, San Francisco, 1969, pp.27–62), using a copoly (styrene-divinylbenzene) containing 0.1–1.0 mMol amines/g polymer.

Reductive alkylation of amino acid aldehydes may be used to introduce reduced amide bonds (—$CR_aR_bNR_c$—) between amino acids A and B and/or D and E. Procedures for reductive alkylation are known in the art. See, e.g., Y. Sasaki and D. H. Coy, Peptides, 8, 119–121 (1987).

When, for example, the compounds of the present invention are synthesized using Merrifield solid phase peptide synthesis as depicted in FIG. 1, Boc-Leucine is loaded onto Merrifield resin (chloromethylated polystyrene 1% divinylbenzene crosslinked, 1.25 meq/g) by reaction with the cesium salt of leucine (from leucine reacted with cesium carbonate) in DMF at 55–60° C. overnight. The final substitution of the resin after loading is 0.95 meq/g. BOP/HOBt/DIEA are then used as coupling reagents to couple amino acids, unless otherwise noted.

Completion of coupling steps is confirmed using Kaiser's ninhydrin test. Washing of the resin after coupling reactions is done with DMF (about 3×1 min), MeOH (about 3×1 min) and CH$_2$Cl$_2$ (about 3×1 min). The reduced amide bonds are protected using benzyl chloroformate. Removal of the Boc-protecting group is done using 50% TFA, 5% anisole in CH$_2$Cl$_2$ (v/v/v) for about 30 min. Resin washing after deprotection was done with CH$_2$Cl$_2$ (about 3×1 min), MeOH (about 3×1 min) and again with CH$_2$Cl$_2$ (about 3×1 min). Antimicrobial compounds are cleaved from the resin and all protecting groups removed using anhydrous HF/5–10% anisole for 1.5 h at 0° C. Antimicrobial compounds are then precipitated with ether, extracted with 25% acetic acid and lyophilized. Further purification of compounds was done using solid phase extraction (Varian Mega Bond-elut C18 loaded syringes).

The compounds can also be purified by such techniques as gel filtration on Sephadex G-15 using 5% acetic acid as a solvent. Lyophilization of appropriate fractions of the column will yield the homogeneous compounds or compound variants, which can then be characterized by such standard techniques such as amino acid analysis, thin layer chromatography, high performance liquid chromatography, ultraviolet absorption spectroscopy, molar rotation, solubility, and mass spectrometry.

In cases where compounds are sufficiently basic or acidic to form stable nontoxic acid or base salts, administration of the compounds as salts may be appropriate. Examples of pharmaceutically acceptable salts are organic acid addition salts formed with acids which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Compounds of the invention can be useful as therapeutic agents for treating infections caused by various yeasts, bacterias, and other agents, including Acinetobacter sp.,

*Alcaligenes faecalis, Citrobacter diversus, Citrobacter freundii, Corynebacterium jeikeium, Enterobacter aerogenes, Enterobacter cloacae, Enterococcus faecalis, Escherichia coli, Klebsiella oxytoca, Klebsiella pneumoniae, Pseudomonas aeruginosa, Pseudomonas fluorescens, Pseudomonas stutzeri, Staphylococcus aureus* (MSSA), *Staphylococcus epidermidis, Staphylococcus haemolyticus, Staphylococcus hominis, Staphylococcus simulans, Staphylococcus warneri, Staphylococcus xylosus, Stenotrophomonas maltophilia, Streptococcus agalactiae, Streptococcus bovis, Streptococcus equinus, Streptococcus pyogenes*, Streptococcus group C, Streptococcus group G, Viridans group streptococci., *Bacteroides fragilis, Bacteroides ovatus, Bacteroides ureolyticus, Bacteroides vulgatus, Clostridium difficile, Clostridium perfringens, Clostridium ramosum, Clostridium sporogenes*, Clostridium sp., *Peptostreptococcus anaerobius, Peptostreptococcus asaccharolyticus,Peptostreptococcus magnus, Prevotella bivia*, and *Prevotella melaninogenica.*

Compounds of the invention can also be used as antiviral and antitumor agents.

Additionally, compounds of the invention may be useful as pharmacologic tools for the further investigation of the pathology of infection.

The compounds of formula (I) can be formulated as pharmaceutical compositions and administered to a mammalian host, such as a human patient in a variety of forms adapted to the chosen route of administration, i.e., orally or parenterally, by intravenous, intramuscular, topical or subcutaneous routes.

The compounds of formula (I) can either be administered alone, with various additives and formulations, or in combination with other known or effective antibiotic agents such as the penicillins, cephalosporins, vancomycins, fluoroquinolones, carbapenems, macrolides, and peptide antibiotics, or with more complex mixtures such as those combining a penicillin with penicillinase inhibitor (Augmentin).

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipient and used in the form of ingestible tablets, buccal tablets, torches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of a given unit dosage form. The amount of active compound in such therapeutically useful compositions is such that an effective dosage level will be obtained.

The tablets, troches, pills, capsules, and the like may also contain the following: binders such as gum tragacanth, acacia, corn starch or gelatin; excipient such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The active compound may also be administered intravenously or intraperitoneally by infusion or injection. Solutions of the active compound or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in pure form, i.e., when they are liquids. However, it will generally be desirable to administer them to the skin as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver the compounds of formula I to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

The compounds of formula (I) can also be delivered by inhalation. Suitable pharmaceutical compositions for inhalation are aerosols with a particle size of from 0.5 μm to 7 μm which enter the compartments of the lungs. Aqueous or aqueous-organic solutions or suspensions which can be nebulized in combination with propelling agents, such as fluoro chloro hydrocarbons, fluorinated hydrocarbons, dimethyl ether, propane, butane, nitrogen, carbon dioxide, $N_2O$, or mixtures of powders with microfine drugs, which can be administered using inhalers are particularly suitable. These pharmaceutical compositions may comprise appropriate additives, such as surface active substances, for instance phospholipids, sorbitane esters, polyoxy sorbitane esters, or oleic acids, alcohols and polyols such as ethanol, glycerol, poly ethylene glycol, glucose, mannitol, sorbitol, in order to improve their relevant pharmaceutical properties.

Useful dosages of the compounds of formula I can be determined by comparing their in vitro activity, and in vivo activity in animal models. Methods for the extrapolation of effective dosages in mice, and other animals, to humans are known to the art; for example, see U.S. Pat. No. 4,938,949.

Generally, the concentration of the compound(s) of formula I in a liquid composition, such as a lotion, will be from about 0.1–25 wt-%, preferably from about 0.5–10 wt-%. The concentration in a semi-solid or solid composition such as a gel or a powder will be about 0.1–5 wt-%, preferably about 0.5–2.5 wt-%.

The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

In general, however, a suitable dose will be in the range of from about 0.5 to about 100 mg/kg, e.g., from about 10 to about 75 mg/kg of body weight per day, such as 3 to about 50 mg per kilogram body weight of the recipient per day, preferably in the range of 6 to 90 mg/kg/day, most preferably in the range of 15 to 60 mg/kg/day.

The compound is conveniently administered in unit dosage form; for example, containing 5 to 1000 mg, conveniently 10 to 750 mg, most conveniently, 50 to 500 mg of active ingredient per unit dosage form.

Ideally, the active ingredient should be administered to achieve peak plasma concentrations of the active compound of from about 0.5 to about 75 μM, preferably, about 1 to 50 μM, most preferably, about 2 to about 30 μM. This may be achieved, for example, by the intravenous injection of a 0.05 to 5% solution of the active ingredient, optionally in saline, or orally administered as a bolus containing about 1–100 mg of the active ingredient. Desirable blood levels may be maintained by continuous infusion to provide about 0.01–5.0 mg/kg/hr or by intermittent infusions containing about 0.4–15 mg/kg of the active ingredient(s).

The desired dose may conveniently be presented in a single dose or as divided doses administered at appropriate intervals, for example, as two; three, four or more sub-doses per day. The sub-dose itself may be further divided, e.g., into a number of discrete loosely spaced administrations; such as multiple inhalations from an insufflator or by application of a plurality of drops into the eye.

The ability of a compound of the invention to act as an antimicrobial agent may be determined using pharmacological models which are well known to the art, or using Test A described below.

EXAMPLES

The invention will now be illustrated by the following non-limiting Examples.

General Methods For Antimicrobial Compound Preparation

Melting points were determined using a Thomas-Hoover capillary melting point apparatus and are uncorrected. Specific optical rotations were determined using a Jasco Model 700 at the sodium D line. Proton Nuclear Magnetic Resonance ($^1H$ NMR) spectra were recorded on a Bruker AMX-500 Fourier Transform (FT) NMR, as well as an INOVA-3 300 MHZ FT NMR. Thin Layer Chromatography (TLC) was performed using silica gel plates (Merck 254) developed in the following solvent systems: (A) ethyl acetate/hexane 1:1, (B) Butanol/acetic acid/water 4:1:1; chloroform/methanol/acetic acid 85:10:5. TLC was visualized using an ultraviolet lamp or 1% ninhydrin spray in ethanol. Reverse phase high pressure liquid chromatography (HPLC) was performed using a Hitachi 655 A-11 equipped with a Vydac $C_{18}$ column (218TP54, 4.6×250 mm), a UV detector (655A), LC controller (L5000) and an integrator/plotter (D-2000). Retention times are given for gradient elution using 5–95% solvent B over 30 min with a flow rate of 1 mL/min in the solvent system (A/B) 0.05% trifluoroacetic acid (TFA) in water/0.05% TFA in acetonitrile. Detection was done at 220 or 254 nm. Mass Spectrometry was done a PE Biosystems Voyager DE-PRO MALDI-TOF mass spectrometer. LC-MS was performed at the Health Science Center at the University of Louisville.

All solvents and reagents were obtained commercially unless otherwise noted. Technical grade dichloromethane ($CH_2Cl_2$) and dimethylformamide (DMF) were purchased from Fisher Scientific and distilled before use. Protected amino acids were purchased from Bachem Bioscience Inc. (King of Prussia, PA.) and Chem-Impex International (IL). Side chain protecting groups were dicholorbenzyloxy for carbonyl, benzyl for Ser, benzylchloroformate (2–Cl-Z) for Lys. TFA was purchased from Halocarbon. Benzotriazole-1-yl-oxy-tris(diethylamino)-phosphonium hexafluorophosphate (BOP) and 1-hydroxybenzotriazole (HOBt) were purchased from Chem-Impex. N, N, N¢, N¢, ¢-Tetramethyl-fluoroformamidinium hexafluorophosphate (TFFH) and was purchased from PE Biosystems. 4-Aminomethylbenzoic acid (4-Amb), N,N-diisopropylethylamine (DIEA), anisole, benzylchloroformate (Z-Cl), lithium aluminum hydride (LAH), and sodium cyanoborohydride ($NaBH_3CN$) were purchased from Adrich Chemical Co. (St. Louis). Anhydrous HF (semiconductor grade) was purchased from Matheson Gas Products, Inc.

All antimicrobial compounds were synthesized manually using fritted syringes as reaction vessels.

Example 1

Synthesis of Boc-Leucine Merrifield Resin

Boc-Leucine was loaded onto Merrifield resin (chloromethylated polystyrene 1% divinylbenzene crosslinked, 1.25 meq/g) by reaction with the Cesium salt of Leucine (from Leucine reacted with cesium carbonate) in DMF at 55–60° C. overnight. The final substitution of the resin after loading was 0.95 meq/g.

Example 2

Synthesis of Boc-protected Amino Acid Aldehydes
a. Synthesis of Boc-Amino Acid-N(OCH$_3$)CH$_3$ where Amino Acid=Phe, 2-Nal 9.5 mmol Boc-Amino Acid-OH was dissolved in 50 mL CH$_2$Cl$_2$ along with 9.5 mmol O, N-dimethylhydroxylamine hydrochloride, 9.5 mmol BOP, and 19 mmol DIEA and reacted for 2 h. The pH was kept at 7–8 by addition of more DIEA over the course of the reaction. The solvent was evaporated, and the resulting residue dissolved in EtOAc. This solution was washed with 1 N HCl (3×30 mL), 10% NaHCO$_3$ (3×30 mL), and saturated NaCl (3×30 mL). The organic layer was dried with MgSO$_4$ and the solvent evaporated to afford an oil.

Boc-Phe-N(OCH$_3$)CH$_3$: 89% yield, Rf (A)=0.64, HPLC RT=24.81 min; $^1$H NMR δ(ppm) 1.41 (s 9H, Boc); 2.85 (dd, 1H, β-H); 3.02 (dd, 1H, β-H); 3.16 (s, 3H, NCH$_3$); 3.67 (s, 3H, NOCH$_3$); 4.91 (dd, 1H, α-H); 7.1–7.3 (m 5H, C$_6$H$_5$).

Boc-2-Nal-N(OCH$_3$)CH$_3$: 75% yield (solid) after recrystallization from EtOAc/hexane. HPLC RT=25.6 min, mp 95–97° C.; 1H NMR δ(ppm) 1.37 (s, 9H, Boc); 3.02 (m, 1H, β-H); 3.17 (s, 3H NCH$_3$); 3.22 (m, 1H, β-H); 3.67 (s, 3H, NOCH$_3$); 5.08 (dd, 1H, α-H);

5.18 (s, 1 h, CONH); 7.23–7.49 (m, 7H C$_{10}$H$_7$).
b. Synthesis of Boc-Amino Acid-H (Amino Acid=Phe, 2-Nal, 4-Amb)

5.0 mmol Boc-Amino Acid-N(OCH$_3$)CH$_3$ was dissolved in dry Et$_2$O with a few drops of THF (to increase solubility) and placed in an ice bath. 6.3 mmol LiAlH$_4$ was added very slowly over 15 min. The reaction was allowed to warm to room temperature over 1 h. The reaction was quenched with 0.1 N HCl very slowly in an ice bath. The organic layer was separated, and the aqueous layer extracted further with EtOAc (3×30 mL). The organic extracts were combined and washed as before and dried over MgSO$_4$. The solvent was evaporated to afford a solid product without further purification.

Boc-Phe-H: mp 79–81° C.; Rf (A)=0.62; 1H NMR δ(ppm) 1.41 (s 9H, Boc): 3.10 (d, 2H, β-H); 4.41 (dd, 1H, α-H); 5.01 (s, 1h, CONH); 7.1–7.3 (m 5H, C6H5); 9.61 (s 1H, CHO).

Boc-2-Nal-H: 67.5% yield; mp 100–102° C.; Rf (A)= 0.76; 1H NMR δ(ppm) 1.37 (s 9H, Boc); 3.26 (d, 2H, β-H); 4.49 (dd, 1H, α-H); 5.18 (s, 1 h, CONH); 7.13–7.67 (m, 7H C10H7); 9.47 (s 1H, CHO).

Boc-4-Amb-H: 8 mmol Boc-4-Amb-N(OCH$_3$)CH$_3$ was prepared as above from 2.0 g Boc-4-Amb-OH. This provided 1.51 g (6.4 mmol) Boc-4-Amb-H. 80% overall yield from Boc-4-Amb; mp 67–68° C.; Rf (A)=0.83; 1H NMR δ(ppm)

Example 3

Synthesis of Boc-PheΨ[CH$_2$NH]Leu-O-resin

Boc-Leucine Merrifield resin (6.0 g, 0.95 meq/g) was swollen in DMF and successively washed with DMF/1% AcOH until the pH of the solvated resin was 5–6. Boc-Phe-H (4.3 g, 17.1 mmol) and NaBH$_3$CN (1.2 g, 18.1 mmol) were each dissolved in 10 mL DMF/0.5% AcOH. These were combined and added to the resin and allowed to react for 1 h. The resin was washed with DMF (3×20 mL), MeOH (2×20 mL) and CH$_2$Cl$_2$ (3×20 mL). The resulting reduced amide bond (secondary amine) was protected with excess Z-Cl and DIEA overnight to afford 6.7 g Boc-Pheylψ [CH$_2$NE]Leu-O-resin (0.76 mmol/g).

Example 4

Synthesis of H-2-Nalψ[CH$_2$NH]ψYyy-Xxx-Pheψ [CH$_2$NH]Leu-OH where Xxx=Ser, Val, or Phle; Yyy=Lys, Met, Ile, Aib, Deg, 3-Amb, or 4-Amb Merrifield solid phase peptide synthesis was used for coupling of amino acids Xxx and Yyy. A 3 times excess of Boc-protected amino acid, BOP, HOBt and 6 times excess of DIEA was used for coupling (1 h). Introduction of 2-Nalψ [CH$_2$NH] was done using the same reductive alkylation step as for the introduction of Pheψ[CH$_2$NH]. The peptides were cleaved from the resin as well as all other protecting groups removed using anhydrous HF (1 h, 0° C.). The compounds were extracted with 25% AcOH and lyophilized.

Example 5

Synthesis of H-2-Nalψ[CH$_2$NH]Zzz-Aaa-Pheψ [CH$_2$NH]Leu-OH, where Aaa=Aib or Deg; Zzz Lys, Met, Ile or Nle The same steps were used as in Item 4, except the coupling of Boc-Aaa-Zzz-Pheψ[CH$_2$NH]Leu-O-resin was different. In this case, TFFH was used as the coupling reagent in place of BOP in the same proportion. All other steps were identical.

Example 6

Synthesis of modified antimicrobial compounds: Derivatives of H-2-Nalψ[CH$_2$NH]Lys-Ser-Pheψ [CH$_2$NH]Leu-OH H-2-Nalψ[CH$_2$NH]Lys-Ser-Pheψ[CH$_2$NH]Leu-OH modified in the following ways: a) using D-amino acids (Boc-D-2-Nal, and all D sequences); acetylation of the N-terminus; b) substitution of 4-Amb for Phe, 2-Nal or both; c) replacing one or more reduced amide bonds with normal peptide bond; d) acetylation of the side chain of Lys.
a. D-Amino Acid Variants The D-amino acid containing compounds were synthesized by replacing the L-amino acids with D-amino acids. Acetylation of the N-terminus was accomplished using excess acetic anhydride and pyridine overnight before final HF cleavage of the compound from the resin. Boc-4-Amb-H was used in place of Boc-Phe-H, Boc-Nal-H or both in the reductive alkylation step(s) of the synthesis. Boc-Phe-OH and Boc-2-Nal-OH were used with the normal amino acid coupling strategy for replacement of the reduced amide bond(s) with normal peptide bonds.
b. Sidechain Variants Acetylation of the side chain of Lys was accomplished using Boc-Lys(Fmoc)-OH in place of the usual 2-ClZ side chain protection. The Fmoc protecting group was removed by treatment with 20% piperidine in DMF for 20 min. The resin was then washed with DMF, then CH$_2$Cl$_2$ as before. Treatment with excess acetic anhydride and DIEA afforded the acetylated side chain. The following steps were the same as previously described.

Example 7

Synthesis of Modified Aantimicrobial Compounds; Derivatives of H-2-Nalψ[CH$_2$NH]Met-Aib-Pheψ [CH$_2$NH]-Leu-OH H-2-Nalψ[CH$_2$NH]Met-Aib-Pheψ[CH$_2$NH]Leu-OH was modified in the following ways: a) using all D-amino acids;

b) acetylation of the reduced amide bond between 2-Nal and Met; c) substitution of Nle for Met; substitution of 3- or 4-Amb for Aib; d) amidation of the C-terminus.

a. D Amino Acid Variants

The all L-amino acid sequences were synthesized exactly the same way as the all D-sequences using D-amino acids. Acetylation of the reduced amide bond was done as previously described. Amidation of the C-terminus was accomplished by using Boc-Leu-O-MBHA resin as the starting material which affords the amide when cleaved rather than the free acid.

Spectral and other physical characterization data for the peptides of the present invention are provided below.

H-2-Nal ψ[CH$_2$NH]Lys-Ser-Pheψ[CH$_2$NH]Leu-OH (1). MW calc'd 662.9; MW Found 663.1. 61% Yield. HPLC RT(min) 16.53.

H-2-Nalψ[CH$_2$NH]Lys-Val-Pheψ[CH$_2$NH]Leu-OH (2). MW calc'd 674.9; MW Found 675.2. 18% Yield 18. HPLC RT(min) 17.40.

H-2-Nalψ[CH$_2$NH]Lys-Phe-Pheψ[CH$_2$NH]Leu-OH (3). MW calc'd 723.0; MW Found 722.9. 18% Yield. HPLC RT(min) 18.27.

H-2-Nalψ[CH$_2$NH]Met-Ser-Pheψ[CH$_2$NH]Leu-OH (4). MW calc'd 665.9; MW Found 666.2. 22 2 Yield. HPLC RT(min) 18.48.

H-2-Nalψ[CH2NH]Met-Val-Pheψ[CH$_2$NH]Leu-OH (5). MW calc'd 677.9; MW Found 678.2.9% Yield. HPLC RT(min) 20.85.

H-2-Nalψ[CH$_2$NH]Met-Phe-Pheψ[CH$_2$NH]Leu-OH (6). MW calc'd 726.0; MW Found 726.1. 8% Yield. HPLC RT(min) 20.85.

H-2-Nalψ[CH$_2$NH]Ile-Ser-Pheψ[CH$_2$NH]Leu-OH (7). MW calc'd 647.9; MW Found 648.2. 10% Yield. HPLC RT(min) 18.36.

H-2-Nalψ[CH$_2$NH]Ile-Val-Pheψ[CH$_2$NH]Leu-OH (8). MW calc'd 659.9; MW Found 660.0. 54% Yield. HPLC RT(min) 19.81.

H-2-Nalψ[CH$_2$NH]Ile-Phe-Pheψ[CH$_2$H]Leu-OH (9). MW calc'd 708.0; MW Found 708.1. 61% Yield. HPLC RT(min) 21.09.

H-2-Nalψ[CH$_2$NH]Aib-Ser-Pheψ[CH$_2$NH]Leu-OH (10). MW calc'd 619.8; MW Found 619.9. 54% Yield. HPLC RT(min) 17.87.

H-2-Nalψ[CH$_2$NH]Aib-Val-Pheψ[CH$_2$NH]Leu-OH (11). MW calc'd 631.9; MW Found 632.1. 84% Yield. HPLC RT(min) 19.43.

H-2-Nalψ[CH$_2$NH]Aib-Phe-Pheψ[CH$_2$NH]Leu-OH (12). MW calc'd 679.9; MW Found 680.3. 63% Yield. HPLC RT(min) 20.36.

H-2-Nalψ[CH$_2$NH]Lys-Aib-Pheψ[CH$_2$NH]Leu-OH (13). MW calc'd 660; MW Found 661.3. 20% Yield. HPLC RT(min) 17.48.

H-2-Nalψ[CH$_2$NH]Met-Aib-Pheψ[CH$_2$NH]Leu-OH (14). MW calc'd 663.9; MW Found 664.2. 81% Yield. HPLC RT(min) 20.59.

H-2-Nalψ[CH$_2$NH]Ile-Aib-Pheψ[CH$_2$NH]Leu-OH (15). MW calc'd 645.9; MW Found 646.2. 16% Yield. HPLC RT(min) 20.42.

H-2-Nalψ[CH$_2$NH]Deg-Ser-Pheψ[CH$_2$NH]Leu-OH (16). MW calc'd 647.9; MW Found 647.9. 16% Yield. HPLC RT(min) 18.70.

H-2-Nalψ[CH$_2$NH]Deg-Val-Pheψ[CH$_2$NH]Leu-OH (17). MW calc'd 660.9; MW Found 660.9. 10% Yield. HPLC RT(min) 18.50.

H-2-Nalψ[CH$_2$NH]Deg-Phe-Pheψ[CH$_2$NH]Leu-OH (18). MW calc'd 708.0; MW Found 707.8. 51 Yield. HPLC RT(min) 21.48.

H-2-Nalψ[CH$_2$NH]Lys-Deg-Pheψ[CH$_2$NH]Leu-OH (19). MW calc'd 689.0; MW Found 689.1. 16% Yield. HPLC RT(min) 17.80.

H-2-Nalψ[CH$_2$NH]Met-Degψ[CH$_2$H]Leu-OH (20). MW calc'd 692.0; MW Found 691.5. 23% Yield. HPLC RT(min) 21.69.

H-2-Nalψ[CH$_2$NH]Ile-Deg-Pheψ[CH$_2$NH]Leu-OH (21). MW calc'd 673.9; MW Found 673.0. 23% Yield. HPLC RT(min) 18.65.

H-D-2-Nalψ[CH$_2$NH]Lys-Ser-Pheψ[CH$_2$NH]Leu-OH (22). MW calc'd 662.9; MW Found 662.6. 80% Yield. HPLC RT(min) 17.33.

H-2-NalΨ[CH$_2$NAc]Lys-Ser-PheΨ[CH$_2$NH]Leu-OH (23). MW calc'd 704.9; MW Found 705.1. 78% Yield. HPLC RT(min) 18.98.

Ac-2-Nalψ[CH$_2$NH]Lys-Ser-Pheψ[CH$_2$NH]Leu-OH (24). MW calc'd 704.9; MW Found 704.5. 97% Yield. HPLC RT(min) 17.91.

H-2-Nalψ[CH$_2$NAc]Met-Aib-PheΨ[CH$_2$NH]Leu-OH (25). MW calc'd 705.9; MW Found 705.4. 10% Yield. HPLC RT(min) 22.11.

H-2-Nal-Lys-Ser-Phe-Leu-OH (26)(SEQ ID NO:1). MW calc'd 690.9. MW Found 690.5. 86% Yield. HPLC RT(min) 18.54.

H-2-Nalψ[CH$_2$NH]Lys-Ser-Phe-Leu-OH (27)(SEQ ID NO:2). MW calc'd 676.9; MW Found 676.3. 48% Yield. HPLC RT(min) 18.26.

H-2-Nalψ[CH$_2$NH]Lys(Ac)-Ser-Pheψ[CH$_2$NH]Leu-OH (28). MW calc'd 704.9; MW Found 705.4. 84% Yield. HPLC RT(min) 17.40.

H-D-2-Nalψ[CH$_2$NH]D-Lys-D-Ser-D-Pheψ[CH$_2$NH]-Leu-OH (29). MW calc'd 662.9; MW Found 662.4. 98% Yield. HPLC RT(min) 16.39.

H-2-Nalψ[CH$_2$NH]Lys-Ser-Pheψ[CH$_2$NAc]Leu-OH (30). MW calc'd 704.9; MW Found 704.4. 85%4 Yield. HPLC RT(min) 19.00.

H-2-Nalψ[CH$_2$NH]Met-Aib-Pheψ[CH-$_2$NH]Leu-NH$_2$ (31). MW calac'd MW Found 662.4 72% Yield. HPLC RT (min) 20.34.

H-2-Nalψ[CH$_2$NH]Nle-Aib-Pheψ[CH$_2$NH]Leu-OH (32). MW calc'd 645.9; MW Found 645.4. 16% Yield. HPLC RT(min) 21.58.

H-2-Nalψ[CH$_2$H]Met-4-AMB-Pheψ[CH$_2$NH]Leu-OH (33). MW calc'd 711.9; MW Found 711.4. 21% Yield. HPLC RT(min) 19.57.

H-2-Nalψ[CH$_2$NH]Met-3-AMB-Pheψ[CH$_2$NH]Leu-OH (34). MW calc'd 711.9; MW Found 711.4. 75% Yield. HPLC RT(min) 20.49.

H-D-2-Nalψ[CH$_2$NH]D-Met-Aib-D-Pheψ[CH$_2$NH]D-Leu-OH (35). MW calc'd 663.9; MW Found 663.4. 29% Yield. HPLC RT(min) 20.59.

H-2-Nalψ[CH$_2$NH]Lys-Ser-4-AMBψ[CH$_2$NH]Leu-OH (36). MW calc'd 648.9; MW Found 648.4. 75% Yield. HPLC RT(min) 14.71.

4-AMBψ[CH$_2$NH]Lys-Ser-Pheψ[CH$_2$NH]Leu-OH (37). MW calc'd 598.8; MW Found 598.4. 92% Yield. HPLC RT(min) 12.39.

4-AMBψ[CH$_2$NH]Lys-Ser-4-AMBψ[CH$_2$NH]Leu-OH (38). MW calc'd 584.9; MW Found 584.4. 89% Yield. HPLC RT(min) 10.16.

The antimicrobial activity of compounds of formula (I) can be determined using Test A.

Test A

The antimicrobial compounds of the present invention were assayed using a standard microdilution assay against gram-positive bacteria *Staphylococcus aureus* (strain used: ATTC 29213) and methicillin-resistant strain used ATCC 33591) and the gram-negative bacteria *Pseudomonas aeruginosa* (strain used ATCC27853). The samples were assayed against 1–5×10⁵ colony forming units, in Mueller-Hinton broth, at 37° C. The activity was determined following a 21 hour incubation. The $IC_{50}$ values were calculated using sigmoidal curve fitting software. (Graphpad™, ISI Software, San Diego, Calif.) and correspond to the sample concentration which inhibits 50 percent of bacterial growth. The minimum inhibitory concenttration (MIC) is defined as the lowest concentration of sample at which no growth is detected by optical density between

TABLE 2

Antimicrobial Assay with *Pseudomonas aeruginosa*

| Structure | $IC_{50}$ | (μg/mL) MIC |
|---|---|---|
| 1 H-Nalψ[CH₂NH]Lys-Ser-Pheψ[CH₂NH]Leu-OH | 10 | 16–32 |
| 14 H-Nalψ[CH₂NH]Met-Aib-Pheψ[CH₂NH]Leu-OH | 20 | 31–62 |
| 3 H-Nalψ[CH₂NH]Lys-Phe-Pheψ[CH₂NH]Leu-OH | 31 | 40–62 |
| 2 H-Nalψ[CH₂NH]Lys-Val-Pheψ[CH₂NH]Leu-OH | 58 | 80–152 |
| 13 H-Nalψ[CH₂NH]Lys-Aib-Pheψ[CH₂NH]Leu-OH | 59 | 80–125 |
| 20 H-Nalψ[CH₂NH]Met-Deg-Pheψ[CH₂NH]Leu-OH | 64 | 80–125 |
| 19 H-Nalψ[CH₂NH]Lys-Deg-Pheψ[CH₂NH]Leu-OH | 143 | 250–500 |
| 16 H-Nalψ[CH₂NH]Deg-Ser-Pheψ[CH₂NH]Leu-OH | 170 | |

As depicted in Table 2, experimental results from Test A for representative compounds of the invention demonstrate that the compounds are active against *Pseudomonas aeruginosa* at $IC_{50}$ and MIC values ranging from 10 ($IC_{50}$) and 16–32 (MIC) for compound 1, to 170 and >250 for compound 16.

Each of the compounds in Table 2 contain two amide bond replacements and are thus linear pseudopeptides. Compounds with unusual amino acids, such as aminoisobutyric acid, (Aib) and diethylglycine (Deg) have also been synthesized and these modifications are also consistent with good potency against the gram negative organism, *Pseudomonas aeruginosa* (e.g., see structures 13, 20, and especially 14). Unusual amino acids such as naphthylalanine or diethylglycine enhance overall hydrophobic character while Aib and Deg may enhance overall stability toward enzymatic degradation (A. F. Spatola, Chemistry and Biochemistry of Amino Acids, Peptides and Proteins, Volume VII, B. Weinstein, ed., 273 (1983)).

TABLE 3

Antimicrobial Assay with Methicillin resistant *Staphylococcus aureus*

| Structure | $IC_{50}$ | (μg/mL) MIC |
|---|---|---|
| 1 H-Nalψ[CH₂NH]Lys-Ser-Pheψ[CH₂NH]Leu-OH | 3 | 8–16 |
| 14 H-Nalψ[CH₂NH]Met-Aib-Pheψ[CH₂NH]Leu-OH | 3 | 8–16 |
| 8 H-Nalψ[CH₂NH]Ile-Val-Pheψ[CH₂NH]Leu-OH | 5 | 8–16 |
| 20 H-Nalψ[CH₂NH]Met-Deg-Pheψ[CH₂NH]Leu-OH | 5 | 16–32 |
| 18 H-Nalψ[CH₂NH]Deg-Phe-Pheψ[CH₂NH]Leu-OH | 6 | 16–32 |
| 9 H-Nalψ[CH₂NH]Ile-Phe-Pheψ[CH₂NH]Leu-OH | 9 | 16–32 |
| 16 H-Nalψ[CH₂NH]Deg-Ser-Pheψ[CH₂NH]Leu-OH | 17 | 62–125 |
| 21 H-Nalψ[CH₂NH]Ile-Deg-Pheψ[CH₂NH]Leu-OH | 34 | 40–162 |
| 3 H-Nalψ[CH₂NH]Lys-Phe-Pheψ[CH₂NH]Leu-OH | 19 | 125–150 |
| 15 H-Nalψ[CH₂NH]Ile-Aib-Pheψ[CH₂NH]Leu-OH | 39 | 80–125 |
| 12 H-Nalψ[CH₂NH]Aib-Phe-Pheψ[CH₂NH]Leu-OH | 26 | 125–250 |
| 6 H-Nalψ[CH₂NH]Met-Phe-Pheψ[CH₂NH]Leu-OH | 44 | 125–250 |
| 13 H-Nalψ[CH₂NH]Lys-Aib-Pheψ[CH₂NH]Leu-OH | 54 | 125–250 |
| 19 H-Nalψ[CH₂NH]Lys-Deg-Pheψ[CH₂NH]Leu-OH | 67 | 125–250 |
| 7 H-Nalψ[CH₂NH]Ile-Ser-Pheψ[CH₂NH]Leu-OH | 69 | 125–250 |
| 2 H-Nalψ[CH₂NH]Lys-Val-Pheψ[CH₂NH]Leu-OH | 69 | 125–250 |

Note:
$IC_{50}$ = concentration of analog required for 50% inhibition of growth.
MIC = minimum concentration of analog required for complete inhibition of growth.

Table 3 provides additional examples of the activities of various pseudopeptides against methicillin resistant *Staphylococcus aureus*. All of these compounds incorporate the residue, 2-naphthylalanine at position 1 and several demonstrate single digit $IC_{50}$ values in this assay. While one of the most active structures contain four positive charges (1), this is not a requirement for activity since compound 14, with only three net positive charges is also active.

Additional assay data for compounds 22–38 are summarized in Table 4.

TABLE 4

Activities of Antimicrobial Peptides 22–38 Against MRSA and *Pseudomonas aeruginosa*

| Compound | Structure | MRSA $IC_{50}$ | Ps A. $IC_{50}$ |
|---|---|---|---|
| 22 | H-D-2-Nalψ[CH₂NH]Lys-Ser-Pheψ[CH₂NH]Leu-OH | 10.9 | 9.2 |
| 23 | H-2-Nalψ[CH₂NAc]Lys-Ser-Pheψ[CH₂NH]Leu-OH | 19.6 | 33.5 |
| 24 | Ac-2-Nalψ[CH₂NH]Lys-Ser-Pheψ[CH₂NH]Leu-OH | 60 | 180 |
| 25 | H-2-Nalψ[CH₂NAc]Met-Aib-Pheψ[CH₂NH]Leu-OH | 28.7 | >500 |
| 26 | H-2-Nal-Lys-Ser-Phe-Leu-OH (SEQ ID NO: 1) | 184 | 388 |
| 27 | H-2-Nalψ[CH₂NH]Lys-Ser-Phe-Leu-OH (SEQ ID NO: 2) | 37.8 | 65.4 |
| 28 | H-2-Nalψ[CH₂NH]Lys(Ac)-Ser-Pheψ[CH₂NH]Leu-OH | 25.8 | 190 |
| 29 | H-D-2-Nalψ[CH₂NH]D-Lys-D-Ser-D-Pheψ[CH₂NH]D-Leu-OH | 18.8 | 13.9 |
| 30 | H-D-2-Nalψ[CH₂NH]Lys-Ser-Pheψ[CH₂NAc]Leu-OH | 26.0 | 50 |
| 31 | H-2-Nalψ[CH₂NH]Met-Aib-Pheψ[CH₂NH]Leu-NH₂ | 10.4 | 94 |
| 32 | H-2-Nalψ[CH₂NH]Nle-Aib-Pheψ[CH₂NH]Leu-OH | 35.0 | >500 |
| 33 | H-2-Nalψ[CH₂NH]Met-4-AMB-Pheψ[CH₂NH]Leu-OH | 17.6 | 163 |
| 34 | H-2-Nalψ[CH₂NH]Met-3-AMB-Pheψ[CH₂NH]Leu-OH | 47.0 | 230 |
| 35 | H-D-2-Nalψ[CH₂NH]D-Met-Aib-D-Pheψ[CH₂NH]D-Leu-OH | 42.1 | 463 |
| 36 | H-2-Nalψ[CH₂NH]Lys-Ser-4-AMBψ[CH₂NH]Leu-OH | 37.5 | 32.2 |

TABLE 4-continued

Activities of Antimicrobial Peptides 22–38 Against MRSA and *Pseudomonas aeruginosa*

| Compound | Structure | MRSA IC$_{50}$ | Ps A. IC$_{50}$ |
|---|---|---|---|
| 37 | 4-AMBψ[CH$_2$NH]Lys-Ser-Pheψ[CH$_2$NH]Leu-OH | >500 | 415 |
| 38 | 4-AMBψ[CH$_2$NH]Lys-Ser-4-AMBψ[CH$_2$NH]Leu-OH | >500 | >500 |

In Table 4, it is shown that some compounds are active against both gram-positive (MRS) and gram negative (*P. aeruginosa*) organisms (e.g., 22 and 23). But it is also possible to modulate activity and selectivity by changes in the composition of the pseudopeptide side chain or backbone structures. Thus compound 33 is quite selective toward MRSA while compound 29 appears to have slight selectivity for the gram-negative organisms. It is also noteworthy that compound 26, with no amide bond replacements, shows modest activity in both assays while analog 25 which carries acetyl protection on one of the amide bond replacement positions and thus has only a net one positive charge, is nevertheless quite active in the MRSA assay and also very selective.

Pharmaceutical Dosage Forms

The following illustrate representative pharmaceutical dosage forms, containing a compound of formula I ('Compound X'), for therapeutic or prophylactic use in humans.

| (I) Tablet 1 | mg/tablet |
|---|---|
| 'Compound X' | 100.0 |
| Lactose | 77.5 |
| Povidone | 15.0 |
| Croscarmellose sodium | 12.0 |
| Microcrystalline cellulose | 92.5 |
| Magnesium stearate | 3.0 |
| | 300.0 |

| (ii) Tablet 2 | mg/tablet |
|---|---|
| 'Compound X' | 20.0 |
| Microcrystalline cellulose | 410.0 |
| Starch | 50.0 |
| Sodium starch glycolate | 15.0 |
| Magnesium stearate | 5.0 |
| | 500.0 |

| (iii) Capsule | mg/capsule |
|---|---|
| 'Compound X' | 10.0 |
| Colloidal silicon dioxide | 1.5 |
| Lactose | 465.5 |
| Pregelatinized starch | 120.0 |
| Magnesium stearate | 3.0 |
| | 600.0 |

| (iv) Injection I (1 mg/ml) | mg/ml |
|---|---|
| 'Compound X' (free acid form) | 1.0 |
| Dibasic sodium phosphate | 12.0 |
| Monobasic sodium phosphate | 0.7 |
| Sodium chloride | 4.5 |
| 1.0 N Sodium hydroxide Solution (pH adjustment to 7.0–7.5) | q.s. |
| Water for injection | q.s. ad 1 mL |

| (v) Injection 2 (10 mg/ml) | mg/ml |
|---|---|
| 'Compound X' (free acid form) | 10.0 |
| Monobasic sodium phosphate | 0.3 |
| Dibasic sodium phosphate | 1.1 |
| Polyethylene glycol 400 | 200.0 |
| 01 N Sodium hydroxide solution (pH adjustment to 7.0–7.5) | q.s. |
| Water for injection | q.s. ad 1 mL |

| (vi) Aerosol | mg/can |
|---|---|
| 'Compound X' | 20.0 |
| Oleic acid | 10.0 |
| Trichloromonofluoromethane | 5,000.0 |
| Dichlorodifluoromethane | 10,000.0 |
| Dichlorotetrafluoroethane | 5,000.0 |

The above formulations may be obtained by conventional procedures well known in the pharmaceutical art.

All publications, patents, and patent documents are incorporated by reference herein, as though individually incorporated by reference. The invention has been described with reference to various specific and preferred embodiments and techniques. However, it should be understood that many variations and modifications may be made while remaining within the spirit and scope of the invention.

We claim:

1. A method of treating or preventing a bacterial infection in a mammal in need thereof, comprising administering to the mammal an effective amount of a compound of formula I:

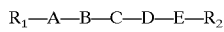

$$R_1—A—B—C—D—E—R_2$$

wherein each of A, B, C, D, and E is independently an amino acid, wherein at least the amide bond connecting A to B is replaced by $—CR_aR_bNR_c—$;

$R_a$, $R_b$, and $R_c$ are each independently hydrogen, ($C_1$–$C_6$) alkyl, ($C_2$–$C_6$)alkenyl, ($C_2$–$C_6$)alkynyl, ($C_3$–$C_8$) cycloalkyl, ($C_1$–$C_6$)alkoxycarbonyl, aryl, or heterocycle; and $R_1$ and $R_2$ are each independently hydrogen, a saccharide, a lipid, a solubilizing agent, or a suitable protecting group;

or a pharmaceutically acceptable salt thereof.

2. The method of claim 1, wherein the amide bond connecting D to E is replaced by $—CR_aR_bNR_c—$.

3. A method of treating or preventing a bacterial infection in a mammal in need thereof, comprising administering to the mammal an effective amount of a compound of formula I:

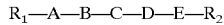

$$R_1—A—B—C—D—E—R_2$$

wherein each of A, B, C, D, and E is independently an amino acid, wherein at least one of the amide (—CONH—) linkages is replaced by $—CR_aC_bR_c—$, and B is an amino acid selected from the group consisting of lysine, methionine, diethylglycine, aminoisobutyric acid, and isoleucine;

$R_a$, $R_b$, and $R_c$ are each independently hydrogen, ($C_1$–$C_6$) alkyl, ($C_2$–$C_6$)alkenyl, ($C_2$–$C_6$)alkynyl, ($C_3$–$C_8$) cycloalkyl, ($C_1$–$C_6$)alkoxycarbonyl, aryl, or heterocycle; and $R_1$ and $R_2$ are each independently hydrogen, a saccharide, a lipid, a solubilizing agent, or a suitable protecting group;

or a pharmaceutically acceptable salt thereof.

4. A method of treating or preventing a bacterial infection in a mammal in need thereof, comprising administering to the mammal an effective amount of a compound of formula I:

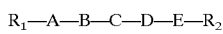

$$R_1—A—B—C—D—E—R_2$$

wherein each of A, B, C, D, and E is independently an amino acid, wherein at least one of the amide (—CONH—) linkages is replaced by $—CR_aR_bR_c—$, and C is an amino acid selected from the group consisting of serine, aminoisobutyric acid, phenylalanine, valine, diethylglycine, and aminomethylbenzoic acid;

$R_a$, $R_b$, and $R_c$ are each independently hydrogen, ($C_1$–$C_6$) alkyl, ($C_2$–$C_6$)alkenyl, ($C_2$–$C_6$)alkynyl, ($C_3$–$C_8$) cycloalkyl, ($C_1$–$C_6$)alkoxycarbonyl, aryl, or heterocycle; and $R_1$ and $R_2$ are each independently hydrogen, a saccharide, a lipid, a solubilizing agent, or a suitable protecting group;

a pharmaceutically acceptable salt thereof.

5. A method of treating or preventing a bacterial infection in a mammal in need thereof, comprising administering to the mammal an effective amount of a compound of formula I:

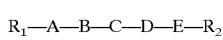

$$R_1—A—B—C—D—E—R_2$$

wherein each of A, B, C, D, and E is independently an amino acid, wherein at least one of the amide (—CONH—) linkages is replaced by $—CR_aR_bR_c—$, and E is leucine;

$R_a$, $R_b$, and $R_c$ are each independently hydrogen, ($C_1$–$C_6$) alkyl, ($C_2$–$C_6$)alkenyl, ($C_2$–$C_6$)alkynyl, ($C_3$–$C_8$) cycloalkyl, ($C_1$–$C_6$)alkoxycarbonyl, aryl, or heterocycle; and $R_1$ and $R_2$ are each independently hydrogen, a saccharide, a lipid, a solubilizing agent, or a suitable protecting group;

or a pharmaceutically acceptable salt thereof.

6. The method of claim 5, wherein A is naphthylalanine or aminomethylbenzoic acid.

7. The method of claim 3, wherein B is lysine or methionine and C is serine or aminomethylbenzoic acid.

8. A method of treating or preventing a bacterial infection in a mammal in need thereof, comprising administering to the mammal an effective amount of a compound of formula I:

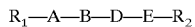

wherein each of A, B, C, D, and E is independently an amino acid, at least one of the amide (—CONH—) linkages is replaced by —CR$_a$R$_b$NR$_c$—, and at least one of A, B, C, D, and E is a D-amino acid;

R$_a$, R$_b$, and R$_c$ are each independently hydrogen, (C$_1$–C$_6$)alkyl, (C$_2$–C$_6$)alkenyl, (C$_2$–C$_6$)alkynyl, (C$_3$–C$_8$)cycloalkyl, (C$_1$–C$_6$)alkoxycarbonyl, aryl, or heterocycle; and R$_1$ and R$_2$ are each independently hydrogen, a saccharide, a lipid, a solubilizing agent, or a suitable protecting group;

or a pharmaceutically acceptable salt thereof.

9. A compound which is H-Nalψ[CH$_2$NH]Aib-Ser-Pheψ[CH$_2$NH]Leu-OH, H-Nalψ[CH$_2$NH]Aib-Val-Pheψ[CH$_2$NH]Leu-OH, H-Nalψ[CH$_2$NH]Aib-Phe-Pheψ[CH$_2$NH]Leu-OH, H-Nalψ[CH$_2$NH]Lys-Aib-Pheψ[CH$_2$NH]Leu-OH, H-Nalψ[CH$_2$NH]Met-Aib-Pheψ[CH$_2$NH]Leu-OH, H-Nalψ[CH$_2$NH]Ile-Aib-Pheψ[CH$_2$NH]Leu-OH, H-Nalψ[CH$_2$NH]Deg-Ser-Pheψ[CH$_2$NH]Leu-OH, H-Nalψ[CH$_2$NH]Deg-Val-Pheψ[CH$_2$NH]Leu-OH, H-Nalψ[CH$_2$NH]Deg-Phe-Pheψ[CH$_2$NH]Leu-OH, H-Nalψ[CH$_2$NH]Lys-Deg-Pheψ[CH$_2$NH]Leu-OH, H-Nalψ[CH$_2$NH]Met-Deg-Pheψ[CH$_2$NH]Leu-OH, H-Nalψ[CH$_2$NH]Ile-Deg-Pheψ[CH$_2$NH]Leu-OH, H-D-2-Nalψ[CH$_2$NH]Lys-Ser-Pheψ[CH$_2$NH]Leu-OH, H-2-Nalψ[CH$_2$NAc]Lys-Ser-Pheψ[CH$_2$NH]Leu-OH, Ac-2-Nalψ[CH$_2$NH]Lys-Ser-Pheψ[CH$_2$NH]Leu-OH, H-2-Nalψ[CH$_2$NAc]Met-Aib-Pheψ[CH$_2$NH]Leu-OH, H-2-Nal-Lys-Ser-Phe-Leu-OH (SEQ ID NO:1), H-2-Nalψ[CH$_2$NH]Lys-Ser-Phe-Leu-OH (SEQ ID NO:2), H-2-Nalψ[CH$_2$NH]Lys(Ac)-Ser-Pheψ[CH$_2$NH]Leu-OH, H-D-2-Nalψ[CH$_2$NH]D-Lys-D-Ser-D-Pheψ[CH$_2$NH]D-Leu-OH, H-2-Nalψ[CH$_2$NH]Lys-Ser-Pheψ[CH$_2$NAc]Leu-OH, H-2-Nalψ[CH$_2$NH]Met-Aib-Pheψ[CH$_2$NH]Leu-NH$_2$, H-2-Nalψ[CH$_2$NH]Nle-Aib-Pheψ[CH$_2$NH]Leu-OH, H-2-Nalψ[CH$_2$NH]Met-4-AMB-Pheψ[CH$_2$NH]Leu-OH, H-2-Nalψ[CH$_2$NH]Met-3-AMB-Pheψ[CH$_2$NH]Leu-OH, H-D-2-Nalψ[CH$_2$NH]D-Met-Aib-D-Pheψ[CH$_2$NH]D-Leu-OH, H-2-Nalψ[CH$_2$NH]Lys-Ser-4-AMBψ[CH$_2$NH]Leu-OH, 4-AMBψ[CH$_2$NH]Lys-Ser-Pheψ[CH$_2$NH]Leu-OH, or 4-AMBψ[CH$_2$NH]-Lys-Ser-4-AMBψ[CH$_2$NH]Leu-OH, or a pharmaceutically acceptable salt thereof.

10. A pharmaceutical composition comprising a compound of claim 9 in combination with a pharmaceutically acceptable diluent or carrier.

11. A compound which is H-2-Nalψ[CH$_2$NH]Aib-Ser-Pheψ[CH$_2$NH]Leu-OH, H-2-Nalψ[CH$_2$NH]Aib-Val-Pheψ[CH$_2$NH]Leu-OH, H-2-Nalψ[CH$_2$NH]Aib-Phe-Pheψ[CH$_2$NH]Leu-OH, H-2-Nalψ[CH$_2$NH]Lys-Aib-Pheψ[CH$_2$NH]Leu-OH, H-2-Nalψ[CH$_2$NH]Met-Aib-Pheψ[CH$_2$NH]Leu-OH, H-2-Nalψ[CH$_2$NH]Ile-Aib-Pheψ[CH$_2$NH]Leu-OH, H-2-Nalψ[CH$_2$NH]Deg-Ser-Pheψ[CH$_2$NH]Leu-OH, H-2-Nalψ[CH$_2$NH]Deg-Val-Pheψ[CH$_2$NH]Leu-OH, H-2-Nalψ[CH$_2$NH]Deg-Phe-Pheψ[CH$_2$NH]Leu-OH, H-2-Nalψ[CH$_2$NH]Lys-Deg-Pheψ[CH$_2$NH]Leu-OH, H-2-Nalψ[CH$_2$NH]Met-Deg-Pheψ[CH$_2$NH]Leu-OH, H-2-Nalψ[CH$_2$NH]Ile-Deg-Pheψ[CH$_2$NH]Leu-OH, or a pharmaceutically acceptable salt thereof.

12. A pharmaceutical composition comprising a compound of claim 11 in combination with a pharmaceutically acceptable diluent or carrier.

\* \* \* \* \*

UNITED STATES PATENT AND TRADEMARK OFFICE
CERTIFICATE OF CORRECTION

PATENT NO.    : 6,551,998 B1
DATED         : April 22, 2003
INVENTOR(S)   : Arno F. Spatola, James J. Wen and David M. Vogel It is certified that error appears in the above-identified patent and that said Letters Patent is hereby corrected as shown below:

<u>Title page,</u>
Item [57], ABSTRACT,
Line 7, delete "—$CR_aR_aR_bNR_c$—" and insert -- —$CR_aR_bNR_c$— -- therefor.

<u>Column 21,</u>
Line 35, delete "wherein at least" and insert -- and -- therefor.
Line 56, delete "—$CR_aC_bR_c$—" and insert -- —$CR_aR_bR_c$— -- therefor.

<u>Column 22,</u>
Line 56, delete "—$CR_aR_bR_c$." and insert -- —$CR_aR_bR_c$— -- therefor.

<u>Column 23,</u>
Line 8, delete "$R_1$—A—B—D—E—$R_2$" and insert -- $R_1$—A—B—C—D—E—$R_2$ -- therefor.

Signed and Sealed this

Twenty-fifth Day of November, 2003

JAMES E. ROGAN
*Director of the United States Patent and Trademark Office*